US00PP28246P3

(12) United States Plant Patent
Aguilar Moran

(10) Patent No.: US PP28,246 P3
(45) Date of Patent: Aug. 8, 2017

(54) BANANA PLANT NAMED 'CQB 115'

(50) Latin Name: ***Musa acuminata×balbisiana* group AAB**
Varietal Denomination: CQB 115

(71) Applicant: Chiquita Brands L.L.C.

(72) Inventor: Juan Fernando Aguilar Moran, La Lima (HN)

(73) Assignee: Chiquita Brands L.L.C., Charlotte, NC (US)

( * ) Notice: Subject to any disclaimer, the term of this patent is extended or adjusted under 35 U.S.C. 154(b) by 337 days.

(21) Appl. No.: 14/120,933

(22) Filed: Jul. 11, 2014

(65) Prior Publication Data

US 2016/0014941 P1 Jan. 14, 2016

(51) Int. Cl.
*A01H 5/08* (2006.01)

(52) U.S. Cl.
USPC ..... Plt./160

(58) Field of Classification Search
USPC ..... Plt./160
CPC ..... A01H 5/08
See application file for complete search history.

*Primary Examiner* — Kent L Bell
(74) *Attorney, Agent, or Firm* — Kilpatrick Townsend & Stockton LLP

(57) ABSTRACT

'CQB 115' is a hybrid dessert banana variety that has a dwarf stature, resistance to black Sigatoka, and produces high-quality fruit.

3 Drawing Sheets

Genus and species: The variety of this invention is botanically identified as *Musa acuminata×balbisiana* group AAB, AA representing two genomes of *M. acuminata* and B representing one genome of *M. balbisiana.*

Variety denomination: The variety denomination is 'CQB 115'.

BACKGROUND OF THE INVENTION

This invention relates to a new and distinctive hybrid banana variety designated as 'CQB 115'. The new hybrid variety was the result of a field cross performed in 2004 in La Lima, Cortes, Honduras between SH-3658×'Pisang Mas' (both unpatented). SH-3648 is a dwarf tetraploid cooking banana resistant to black Sigatoka leaf spot disease, developed from accessions and breeding lines that are unpatented and are in a La Lima, Cortes, Honduras germplasm collection. The pedigree of SH-3648 is II-408 and I-63→SH-2952×SH-2741→SH-3386×SH-3362→SH-3648. The two original II-408 and I-63 parental lines are the 'Gaddatu' (ABB) triploid clone from the Philippines and a *Musa balbisiana* (BB) diploid clone of unknown origin that was collected in Costa Rica. SH-2741 is a dwarf, bred diploid that was derived from AVP-45×AVP-23→SH-90×II-334→SH-2518×II-158→SH-2741. The AVP-45, AVP-23, II-334 and II-158 parental lines are a wild *Musa acuminata* subsp. *zebrina* diploid accession from Java, a 'Robusta' Cavendish triploid clone that was collected in Jamaica, a wild *Musa acuminata* subsp. *siamea* diploid from Malaysia, and a parthenocarpic *Musa acuminata* subsp. *errans* diploid from North Borneo, respectively. The male parent, 'Pisang Mas', is a naturally occurring diploid (AA). 'Pisang Mas' produces small bunches and very sweet-flavored fingers, which are eaten fresh or used as dessert and are sweeter than the common Cavendish banana.

'CQB 115' was selected in 2009 from several first-generation seedlings from the cross between SH-3658 and 'Pisang Mas'. It was selected as a triploid hybrid that maintained the dwarf plant stature and black Sigatoka leaf spot disease-resistance of its SH-3648 female parental line and produced bunches of 20 kilograms with fruits of the same quality of the male 'Pisang Mas' parental line.

'CQB 115' was asexually reproduced by corms by the inventor at the experimental farm in La Lima, Cortés, Honduras. All plant and fruit characteristics run true to the original selected plant and are identical in all aspects.

BRIEF SUMMARY OF VARIETY DESCRIPTION

'CQB 115' is a hybrid dessert banana variety that has a dwarf stature, resistance to black Sigatoka, and produces high-quality fruit.

BRIEF DESCRIPTION OF THE PHOTOGRAPHS

The Figures depict various characteristics of the 'CQB 115' hybrid banana variety. The colors shown in the photographs are as nearly true as is reasonably possible in color representations of this type.

Figures 4A, 4B:
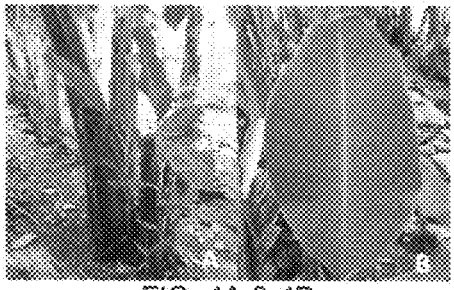

FIG. 4A-B show water suckers (A) and leaves without blotches (B).

Figure 5:
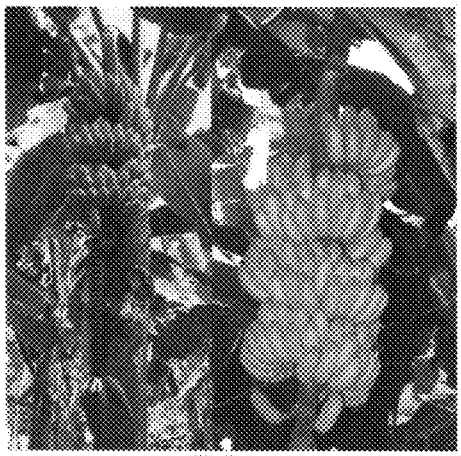

FIG. 5 shows a typical fruit bunch.

Figure 6:
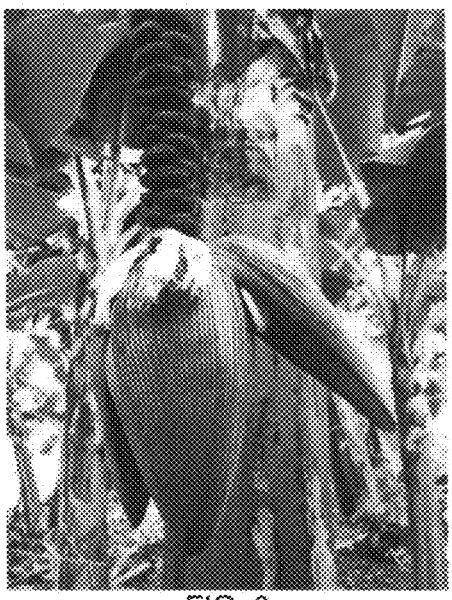

FIG. 6 shows male buds.

Figure 7:
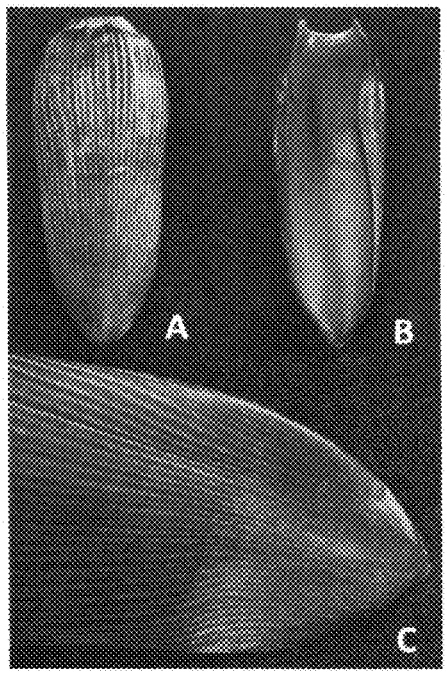

FIG. 7A-C shows bracts of a male bud.

Figure 8:
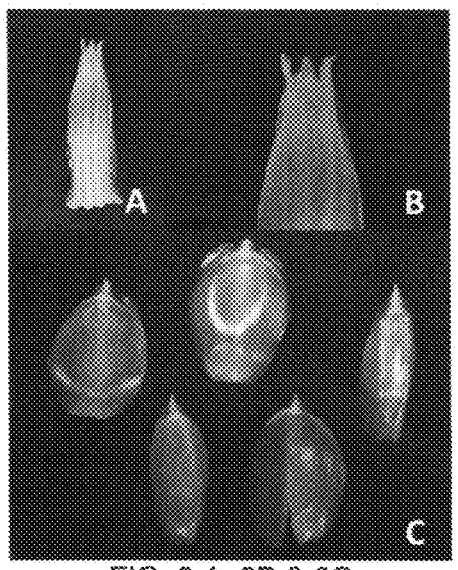

FIG. 8A-C shows lobes of compound tepals (A and B) and free tepals (C).

Figure 9:
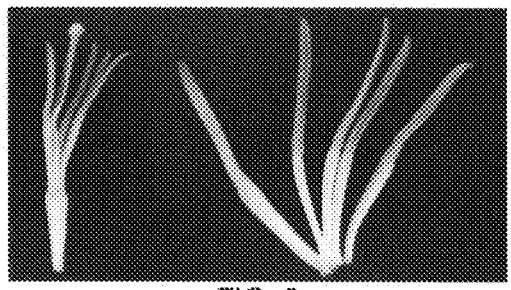

FIG. 9 shows stamens without pollen.

Figures 10A, 10B:
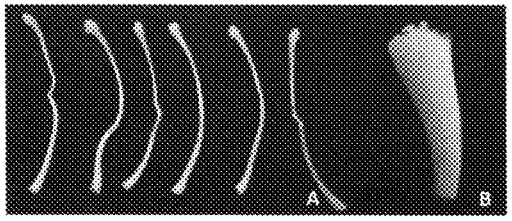

FIG. 10A-B shows the style shape (A) and an ovary (B).

Figure 11:
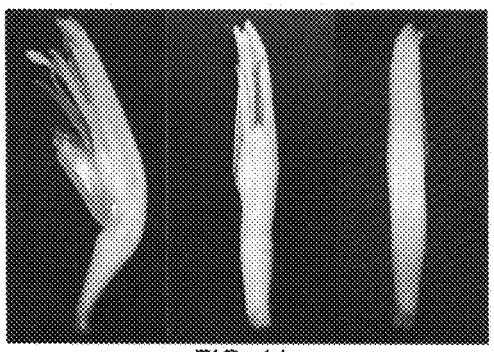

FIG. 11 shows a male flower.

Figure 12:
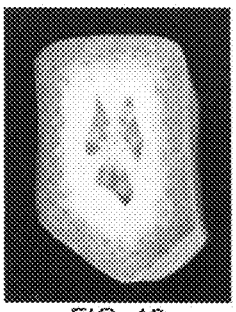

FIG. 12 shows rowed ovules.

Figure 13:
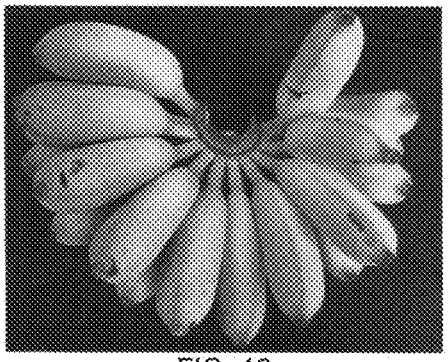

FIG. 13 shows a typical middle hand.

Figures 14A, 14B, 14C:
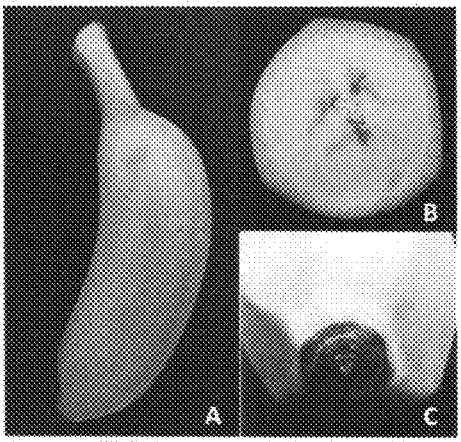

FIG. 14A-C shows the finger shape (A); a transverse section of fruit (B); and the fruit apex (C).

Figure 15:
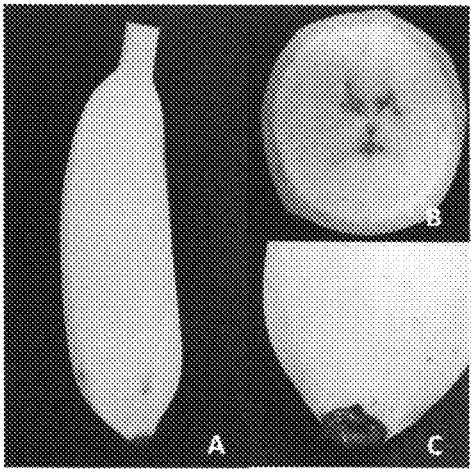

FIG. 15 shows a mature fruit peel (A), mature pulp (B), and mature fruit apex (C).

DETAILED DESCRIPTION OF THE INVENTION

'CQB 115' differs from its male parent 'Pisang Mas' as follows: 'Pisang Mas' is a diploid (2n) plant whereas 'CQB 115' is a triploid (3n). 'CQB 115' also has a dwarf stature compared to 'Pisang Mas'.

'CQB 115' differs from its female parent SH-3648 as follows: SH-3648 is tetraploid (4n) whereas 'CQB 115' is triploid (3n). 'CQB 115' also produces dessert-quality fruit.

'CQB 115' differs from the common Cavendish variety in its resistance to black Sigatoka leaf spot disease.

The following is a detailed botanical description of the new variety 'CQB 115'. The description is from plants located in Limón, Costa Rica that were evaluated between 2013 and 2014. The Ratooning Index is from data collected in an experimental plot located in El Progreso, Honduras. Colors are described using the Munsell Color Chart for Plant Tissues. The descriptions are in accordance with the internationally standardized "Descriptors for Banana (*Musa* spp.)" elaborated by IPGRI-INIBAP/CIRAD, 1996.

The 'CQB 115' plant and its fruit may vary slightly from the detailed descriptors shown below due to cultural practices, soil types and climatic conditions under which the variety may be grown.

TABLE 1

Figure 1:
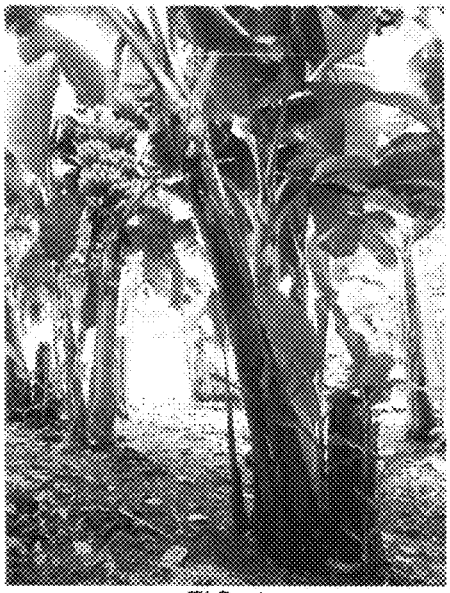
FIG. 1 shows the typical appearance of a plant.
Figures 3A, 3B, 3C:
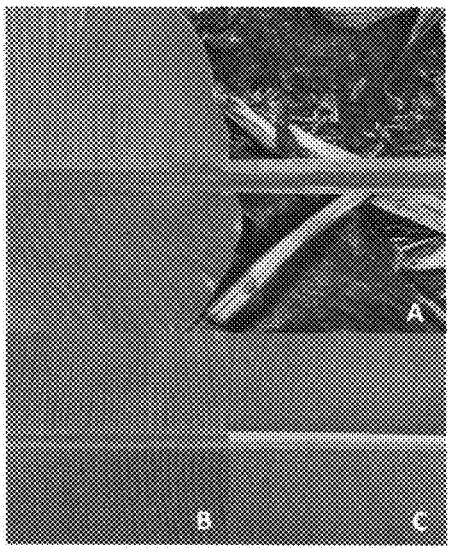
FIG. 3 shows the shape of a leaf blade base (A) and leaf upper (B) and lower (C) surfaces.
Figure 2:
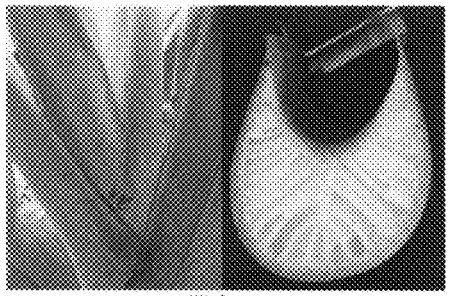
FIG. 2 shows blotches at the petiole base and a petiole canal leaf I.

| Detailed Descriptors | |
|---|---|
| 6.1 1 | Leaf habit: drooping (FIG. 1). |
| 6.1.2 | Dwarfism: dwarf type, leaves strongly overlapped and leaf ratio is 3.15 (278/88 cm) |
| 6.2.1 | Pseudostem height: ≥3.0 m (3.46 m at flowering) |
| 6.2.2 | Pseudostem aspect: robust (83.0 cm) |
| 6.2.3 | Pseudostem colour: 5Y5/6 |
| 6.2.4 | Pseudostem appearance: shinny (not waxy) |
| 6.2.5 | Predominat underlying colour of the pseudostem: 10R5/6 |
| 6.2.6 | Pigmentation of the underlying pseudostem: 10R6/6 |
| 6.2.7 | Sap colour: Watery, not translucent |
| 6.2.8 | Wax on leaf sheaths: very little wax |
| 6.2.9 | Number of suckers: six or seven suckers |
| 6.2.10 | Development of suckers: more than ¾ of the height of the parent plant (FIG. 1) |
| 6.2.11 | Position of suckers: close to parent growing (vertical growth) (FIG. 4A) |
| 6.3.1 | Blotches at the petiole base: extensive pigmentation (FIG. 2). |
| 6.3.2 | Blotches colour: 10R3/6 |
| 6.3.3 | Petiole canal leaf III: open with margins spreading (FIG. 2). |
| 6.3.4 | Petiole margins: winged and clasping the pseudostem (FIG. 2) |
| 6.3.5 | Wing type: dry |
| 6.3.6 | Petiole margin colour: 2.5GY7/6 |
| 6.3.7 | Edge of the petiole margin: with a colour line along (2.5R4/4) |
| 6.3.8 | Petiole margin width: <1 cm |
| 6.3.9 | Leaf blade length: around 278.0 cm |
| 6.3.10 | Leaf blade width: around 88.0 cm |
| 6.3.10.1 | Leaf ratio: ≥3 (around 3.16) |
| 6.3.11 | Petiole length: 70.0 cm |
| 6.3.12 | Colour of leaf upper surface: 5GY3/4 (FIG. 3B) |
| 6.3.13 | Appearance of leaf upper surface: dull (FIG. 3C) |
| 6.3.14 | Colour of the leaf lower surface: 5GY4/4 (FIG. 3C) |
| 6.3.15 | Appearance of the leaf lower surface: dull (FIG. 3C). |
| 6.3.16 | Wax on leaves: very little or no visible signs of wax |

TABLE 1-continued

| Detailed Descriptors | |
|---|---|
| 6.3.17 | Insertion point of leave blades on petiole: asymmetric (FIG. 3A). |
| 6.3.18 | Shape of leave blade: both sides rounded (FIG. 3A). |
| 6.3.19 | Leaf corrugation: even, smooth |
| 6.3.20 | Colour of midrib dorsal surface: 5GY5/4 (FIG. 3B). |
| 6.3.21 | Colour of midrib ventral surface: between 2.5GY7/6 (FIG. 3C). |
| 6.3.22 | Colour of cigar leaf dorsal surface: 2.5GY5/4. |
| 6.3.23 | Blotches on leaves of water suckers: without blotches (FIG. 4B) |
| 6.4.1 | Peduncle length: 89 cm. |
| 6.4.2 | Empty nodes on peduncle: 2 |
| 6.4.3 | Peduncle width: 24.5 cm |
| 6.4.4 | Peduncle colour: 5GY5/6 |
| 6.4.5 | Peduncle hairiness: hairless |
| 6.4.6 | Bunch Position: hanging vertically (bunch ready for harvest) |
| 6.4.7 | Bunch shape: cylindrical (FIG. 5) |
| 6.4.8 | Bunch appearance: very compact (one cannot place one's finger between the hands of the fruit) (FIG. 5) |
| 6.4.9 | Flowers that form the fruit: female |
| 6.4.10 | Fruits: bi-seriate |
| 6.4.11 | Rachis type: present and male but may be degenerated or persistent (FIG. 6) |
| 6.4.12 | Rachis position: falling vertically |
| 6.4.13 | Rachis appearance: neutral flowers |
| 6.4.14 | Male bud type: normal present (FIG. 6) |
| 6.4.15 | Male bud shape: like a top (FIG. 6) |
| 6.4.16 | Male bud size: length 21.5 cm and diameter 29.5 cm (at the widest section) |
| 6.5.1 | Bract base shape: small shoulder (FIG. 7A) |
| 6.5.2 | Bract apex shape: obtuse (FIG. 7C) |
| 6.5.3 | Bract imbrication: young bracts slightly overlap (FIG. 6). |
| 6.5.4 | Color of bract external face: 5R3/4 (FIG. 7A). |
| 6.5.5 | Colour of the bract internal face: 5R4/8 (FIG. 7B). |
| 6.5.6 | Colour on the bract apex: tinted with yellow. |
| 6.5.7 | Colour stripes on bract: with discoloured lines on external face (FIG. 7C) |
| 6.5.8 | Bract scars on rachis: very prominent |
| 6.5.9 | Fading of colour on bract base: colour homogenous (pigmentation is uniform and continues until the base (FIG. 7C) |
| 6.5.10 | Male bract shape: lanceolate x/y ≤ 0.28 (5/20,6 = 0.24) |
| 6.5.11 | Male bract lifting: lifting two or more at the time (FIG. 6) |
| 6.5.12 | Bract behavior before falling: revolute (rolling) (FIG. 6) |
| 6.5 13 | Wax on the bract: very little wax |
| 6.5.14 | Presence of grooves on the bract: moderate grooving (parallel bridges are distinguishable) |
| 6.6.1 | Male flower behavior: falling before the bract. |
| 6.6.2 | Compound tepal basic colour: 2.5Y8/4 (FIG. 8C) |
| 6.6.3 | Compound tepal pigmentation: very few or no visible sign of pigmentation (FIG. 8C) |
| 6.6.4 | Lobe colour of compound tepal: 2.5Y8/10 (FIG. 8C) |
| 6.6.5 | Lobe development of compound tepal: developed (FIG. 8C) |
| 6.6.6 | Free tepal colour: translucent (FIG. 8A) |
| 6.6.7 | Free tepal shape: oval (FIG. 8A) |
| 6.6.8 | Free tepal appearance: simple folding under apex (FIG. 8A) |
| 6.6.9 | Free tepal apex development: developed (FIG. 8B) |
| 6.6.10 | Free tepal apex shape: thread-like (FIG. 8B) |
| 6.6.11 | Anther exertion: exerted (FIG. 9) |
| 6.6.12 | Filament colour: white |
| 6.6.13 | Anther colour: 2.5Y8/2 |
| 6.6.14 | Pollen sac colour: 2.5YR5/4 |
| 6.6.16 | Style basic colour: white (FIG. 10A) |
| 6.6.17 | Pigmentation on style: without pigmentation |
| 6.6.18 | Style exertion: inserted (FIG. 10A) |
| 6.6.19 | Style shape: curved in the middle (FIG. 10A) |
| 6.6.20 | Stigma colour: 7.5YR7/6 (FIG. 10A) |
| 6.6.21 | Ovary shape: slightly arched (FIG. 10B) |
| 6.6.22 | Ovary basic colour: 5Y8/4 (FIG. 10B) |
| 6.6.23 | Ovary pigmentation: very few or no visible sign of pigmentation (FIG. 10B). |
| 6.6.24 | Dominant colour of male flower: light yellow (FIG. 11) |
| 6.6.26 | Arrangement of ovules: two rowed (FIG. 12) |
| 6.7.1 | Fruit position: curved upward 45° or more (based on the mid-hand of the bunch) |
| 6.7.2 | Number of fruits in the mid-hand of the bunch: 20 (FIG. 13) |
| 6.7.3 | Fruit length: 15 cm (FIG. 14A) |
| 6.7.4 | Fruit shape: slightly curved (FIG. 14A) |

TABLE 1-continued

| Detailed Descriptors | |
|---|---|
| 6.7.5 | Transverse section of fruit: slightly ridged (FIG. 14B) |
| 6.7.6 | Fruit apex: pointed (FIG. 14C) |
| 6.7.7 | Remains of flower relicts at fruit apex: base of the style prominent |
| 6.7.8 | Fruit pedicel length: 40 mm |
| 6.7.9 | Fruit pedicel width: 10 mm |
| 6.7.10 | Pedicel surface: hairless |
| 6.7.11 | Fusion of pedicels: very partially or no visible sign of fusion |
| 6.7.12 | Immature fruit peel colour: 5GY7/6 (FIG. 14A) |
| 6.7.13 | Mature fruit peel colour: close to bright yellow (Table B, IPGRI-INIBAP/CIRAD, 1996) |
| 6.7.14 | Fruit peel thickness: 3 mm |
| 6.7.15 | Adherence of the fruit peel: Fruit peels easily |
| 6.7.16 | Crack in fruit peel: without cracks (ripening under experimental conditions) |
| 6.7.17 | Pulp in fruit: with pulp |
| 6.7.18 | Pulp colour before maturity: 2.5Y8/4 |
| 6.7.19 | Pulp colour at maturity: close to yellow (Table B, IPGRI-INIBAP/CIRAD 1996) |
| 6.7.20 | Fruit fall from hands: Persistent |
| 6.7.21 | Flesh texture: Soft (ripening under experimental conditions) |
| 6.7.22 | Predominant taste: Sweet and acid |
| 6.7.23 | Presence of seeds with source of pollen: no |

TABLE 1-continued

| Detailed Descriptors | |
|---|---|
| 6.7.24 | Seed surface: not applicable |
| 6.7.25 | Seed shape: not applicable |

TABLE 2

| Additional fruit, flowering, and harvest descriptors Data from the first production cycle |
|---|
| Days for planting to first flowering: 262.28 |
| Number of leaves at flowering: 14.12 |
| Number of leaves at harvest: 11.36 |
| Days from flowering until harvest: 52.46 |
| Bunch weight (Kg): 16.15 |
| Number of hands: 6.60 |
| Finger diameter (1/32"): 13.32 |
| Days from first flowering until the second one: 236.63 |
| Index of ratooning; 1.54 |

What is claimed is:

1. A new and distinct banana plant having the characteristics substantially as described and illustrated herein.

* * * * *